(12) United States Patent
Yip et al.

(10) Patent No.: US 9,398,972 B2
(45) Date of Patent: Jul. 26, 2016

(54) POSTURE CORRECTION GIRDLE AND THE METHOD OF CORRECTING SPINAL DEFORMITY

(71) Applicant: The Hong Kong Polytechnic University, Hung Hom (HK)

(72) Inventors: Yiu Wan Joanne Yip, Kowloon (HK); Kit Lun Yick, Kowloon (HK); Chi Yung Tse, Kowloon (HK); Chun Wah Marcus Yuen, Kowloon (HK); Sun Pui Ng, Kowloon (HK); Pak Yiu Liu, Kowloon (HK); Ka Ming Law, Kowloon (HK)

(73) Assignee: The Hong Kong Polytechnic University, Hong Kong (CN)

( * ) Notice: Subject to any disclaimer, the term of this patent is extended or adjusted under 35 U.S.C. 154(b) by 256 days.

(21) Appl. No.: 13/858,086

(22) Filed: Apr. 7, 2013

(65) Prior Publication Data
US 2014/0303535 A1    Oct. 9, 2014

(51) Int. Cl.
*A61F 5/00*     (2006.01)
*A61F 5/02*     (2006.01)

(52) U.S. Cl.
CPC .. *A61F 5/02* (2013.01); *A61F 5/026* (2013.01)

(58) Field of Classification Search
CPC ......... A61F 5/026; A61F 5/0102; A61F 2/78; A61F 2/80; A61F 5/028; A61F 2002/5018; A61F 2002/502; A61F 2002/5026; A61F 2002/608; A61F 2002/7862; A61F 2002/7881; A61F 2/60; A61F 2/601; A41D 13/015; A41D 13/0015; A41D 13/0543; A41D 2600/10; A41D 13/0058; A41D 13/05; A41D 13/0512; A41D 1/002; A41D 2400/38; A41D 13/0518; A41D 13/0531; A41D 13/0593; A41D 13/065; A41D 13/0051; A41D 13/1281; A41D 27/00; A41D 13/018; A41D 13/1236; A41D 1/00; A41D 1/005; A41D 31/0038; A63B 24/0062; A63B 53/00; A63B 71/06; A63B 2220/40; A63B 2102/02; A61N 1/0556; A61N 1/3601; A61N 1/37229; A61N 1/0558; A61N 1/3606; A61N 1/3611; A61N 1/36139; A61N 1/3615; A61N 1/37235; A61N 1/3758; A61M 2205/3372; A61M 2205/3389; A61M 5/14244
USPC ...................................... 602/19; 128/874–875
See application file for complete search history.

(56) References Cited

U.S. PATENT DOCUMENTS 2,210,244 A    8/1940   Keith et. al.
2,333,225 A    11/1943  Allen et. al.
(Continued)

*Primary Examiner* — Michael Brown
(74) *Attorney, Agent, or Firm* — Eagle IP Limited; Jacqueline C. Lui

(57) ABSTRACT

A posture correction girdle comprises a body wrapping shell, a plurality of pockets and a plurality of paddings is disclosed. The paddings are configured to be inserted into pockets at predetermined positions. Thereby, when the posture correction girdle is worn by the user, pressure is exerted onto a corresponding predetermined section of the user's spine for posture correction purpose. The posture correction girdle further comprises a pair of elastic shoulder straps, an elastic waist strap and a plurality of elongated bones to provide additional support to the user's spine. A micro-system comprising a processor, an output device and a plurality of sensors can also be embedded into the posture correction girdle to provide information regarding the efficiency of the posture correction girdle and the progression of the treatment. Such information is provided to the users using the output device.

18 Claims, 5 Drawing Sheets

(56) References Cited

U.S. PATENT DOCUMENTS

| | | | |
|---|---|---|---|
| 3,116,735 | A | 1/1964 | Geisner et. al. |
| 3,292,616 | A | 12/1966 | Freeman et. al. |
| 4,730,625 | A | 3/1988 | Fraser et al. |
| 5,072,725 | A * | 12/1991 | Miller ............... 602/19 |
| 5,599,286 | A | 2/1997 | Dansereau |
| 6,283,124 | B1 * | 9/2001 | Schleuning et al. .......... 128/845 |
| D499,806 | S | 12/2004 | Machin et al. |
| 7,842,000 | B2 | 11/2010 | Lai et al. |
| 8,007,457 | B2 | 8/2011 | Taylor |
| 2003/0144622 | A1 | 7/2003 | Kylberg |
| 2005/0070830 | A1 * | 3/2005 | Schultz ............... 602/19 |
| 2005/0197607 | A1 * | 9/2005 | Brown ............... 602/19 |
| 2008/0045873 | A1 | 2/2008 | Zours |
| 2008/0287770 | A1 * | 11/2008 | Kurzweil et al. ............. 600/388 |
| 2008/0313793 | A1 * | 12/2008 | Skottheim et al. ................ 2/461 |
| 2009/0047645 | A1 * | 2/2009 | Dibenedetto et al. ......... 434/258 |
| 2010/0217166 | A1 | 8/2010 | Mills |
| 2010/0256717 | A1 | 10/2010 | Brown |
| 2011/0203029 | A1 | 8/2011 | Okamoto et al. |
| 2011/0213283 | A1 | 9/2011 | Brown |
| 2012/0022420 | A1 | 1/2012 | Sandifer et al. |

\* cited by examiner

POSTURE CORRECTION GIRDLE AND THE METHOD OF CORRECTING SPINAL DEFORMITY

FIELD OF INVENTION

This invention relates to a posture correction girdle and in particular a posture correction girdle for adolescents with early scoliosis.

BACKGROUND OF INVENTION

Adolescent Idiopathic scoliosis (AIS) is a multi-factorial, three-dimensional deformity of the spine and trunk which appears and sometimes progresses during any of the rapid periods of growth in apparently healthy children.

Severe spinal deformities can greatly reduce pulmonary and cardiac functions which may lead to death from cardiopulmonary failure. Therefore, surgery is generally suggested when the curvature of the spine is greater than 45-50 degrees. Non-surgery treatment, such as immobilization with a spinal cast or brace, has been and remained an important treatment modality for adolescent patients that have moderate scoliosis with a curve of 20-45 degrees to prevent curve progression and reduce deformity. Nevertheless, if the curve is less than 20 degrees, even if the child is at a high risk of progressive spinal deformity during the age of 10-16 at puberty, treatment is nothing more than just observation.

Apart from the aforesaid, the adverse psychological impact of spinal casts or braces on patients and its poor compliance has been a well-recognized problem in the field. It is suggested that these spinal casts or braces must be worn for up to 23 hours per day until the child has completed growth (for probably 4-6 years) to be effective. Due to discomfort, activity limitations and unacceptable appearance of the brace, only a small number of teenage patients fully comply with the treatment, and thus adversely affect its effectiveness and progression.

SUMMARY OF INVENTION

In the light of the foregoing background, it is an object of the present invention to provide an alternative design of the posture correction girdle to improve patient compliance. In one preferred embodiment, the posture correction girdle provides adequate support to the user's spine on a daily basis.

Accordingly, the present invention, in one aspect, is a posture correction girdle comprising a body wrapping shell having a plurality of pockets provided therein at predetermined positions and a plurality of paddings. The paddings are provided to be inserted into preselected pockets. When the posture correction girdle is worn by a user, pressure is exerted onto the corresponding predetermined sections of the user's spine for posture correction purpose.

In one embodiment of the present invention, the posture correction girdle further comprises a pair of elastic shoulder straps and/or an elastic waist strap.

In another embodiment, the posture correction girdle further comprises a plurality of elongated bones longitudinally disposed from the top portion to the bottom portion of the body wrapping shell.

According to another aspect of the present invention, it is a posture correction girdle comprising a body wrapping shell with at least one sensor disposed therein, a processor and an output device. The processor is provided to receive and process the signal received from the sensor. The user will be notified of any received signal deviated from the predetermined value by the output device.

In one embodiment, the sensors disposed on the body wrapping shell can be temperature sensor, pressure sensor and/or displacement sensor.

In another aspect, there is provided a method for correction of spinal deformity which comprises the step of providing a posture correction girdle, wrapping the posture correction girdle around a user and selectively exerting pressure onto predetermined sections of the user's spine through the posture correction girdle. Using this method, corrective forces are exerted on that particular predetermined spine section to achieve posture correction, curve reduction, curve progressing prevention or curve progressing delay purposes.

In another embodiment, the method further includes a step of electronically monitoring and providing feedback to the user regarding the efficiency of the correction method.

There are many advantages to the present invention. Comparing with existing posture correction orthoses, the present invention provides a high customizability and flexibility for posture correction treatment. Instead of providing a fixed and rigid orthoses, the paddings of the present invention can be inserted into preselected pockets independently. Moreover, the position of the paddings can be adjusted according to the progression of the treatment when necessary. Thereby, individualized, yet adjustable, treatment regime is provided by exerting an optimal pressure profile onto the user's spine throughout the treatment.

Another advantage of the present invention is that the sensors disposed on the posture correction girdle can provide quantitative parameters regarding the efficiency of the posture correction girdle and thus the treatment. With the aid of these parameters, the physicians can ensure optimal treatment is provided in various stages of the treatment.

Finally, the posture correction girdle and the wrapping shell of the present invention are made of textile materials which lead to less skin irritation and discomfort comparing with thermoplastic or metal orthoses. Thereby the present invention provides a higher patient compliance.

These advantages of the present invention are of great clinical values. As the patients need to wear the posture correction girdle until bone mature (usually patients wear the girdle for 2-5 years), a highly customizable and flexible posture correction girdle with quantitative feedback and high compliance not only enables physicians to provide the optimal treatment, but also more importantly prevents further spinal deformation of AIS patients which can be fatal.

BRIEF DESCRIPTION OF FIGURES

FIG. 1b is a perspective view of the paddings showing some exemplary shapes which correspond to the shape of the pockets of the posture correction girdle shown in the same embodiment of FIG. 1a.

DETAILED DESCRIPTION OF THE PREFERRED EMBODIMENTS

As used herein and in the claims, "comprising" means including the following elements but not excluding others.

As used herein and in the claims, "sagittal plane" is a vertical plane which passes from the front to the rear of a human body and divides the body into left and right halves while "coronal plane" is a vertical plane which divides the body into front and rear sections. The "maxillary line" and the "dorsal line" are the imaginary line on the coronal plane and sagittal plane respectively.

Figure 1A:
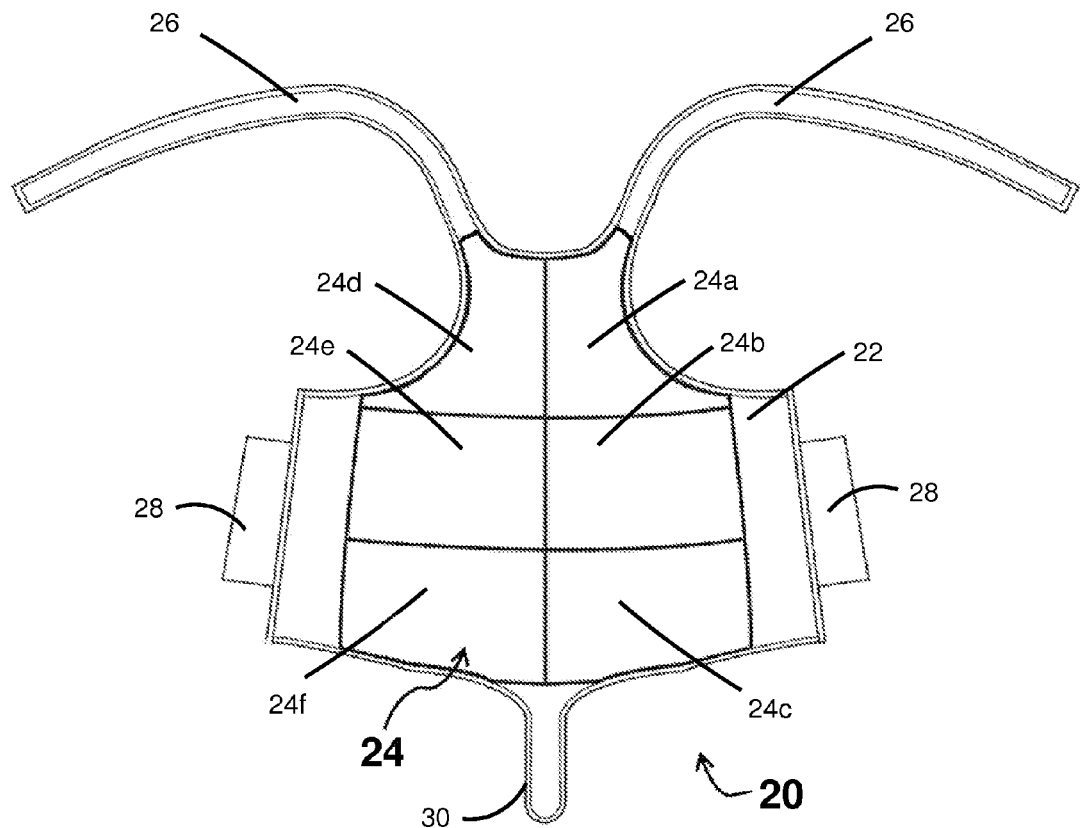
FIG. 1a is a front perspective view of the posture correction girdle in a fully open position showing the inner side according to one embodiment of the present invention.
Figure 1B:
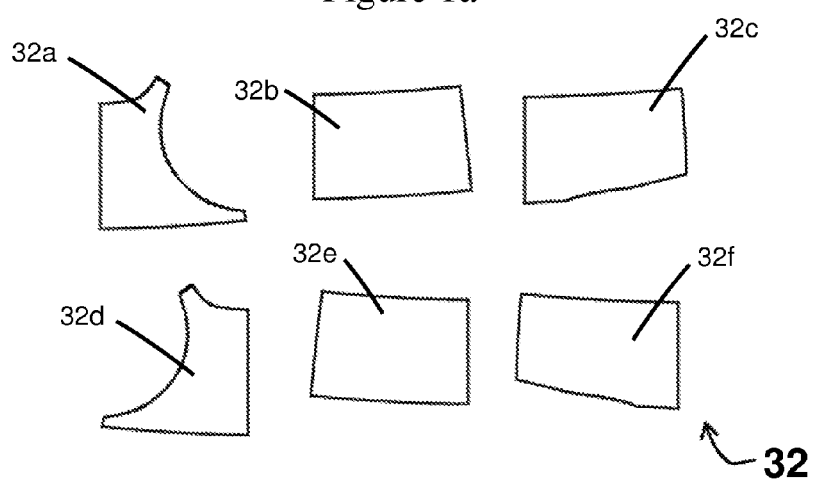

Referring now to FIGS. 1a and 1b, the posture correction girdle 20 according to one aspect of the present invention includes a body wrapping shell 22, a plurality of pockets 24 and a plurality of paddings 32. The body wrapping shell 22 has a front portion and a back portion intended to wrap around the front and back of a user respectively. The back portion of the body wrapping shell 22 is further divided into an upper portion corresponding to the upper back of the user; a middle portion corresponding to the waist of the user and a lower portion corresponding to the lower back and pelvis of the user when the posture correction girdle 20 is worn. In the embodiment shown, the pockets 24 are sewn onto the inner surface of the back portion of body wrapping shell 22 and arranged into six portions. There is a pair of pockets 24 in each of the upper portion, middle portion and lower portion of the body wrapping shell 22 respectively. The shape of each pocket within the pair is a mirror image of the other, and disposed between left and right symmetrically.

As shown in FIG. 1b, the shapes of the paddings 32 are conformed to the shape of corresponding pockets 24. In this embodiment, paddings 32a, 32b, 32c, 32d, 32e, 32f are configured to be independently inserted into pockets 24a, 24b, 24c, 24d, 24e, 24f respectively. Such design allows selective insertion of paddings 32 in preselected pockets 24 according to the spinal deformity of each patent to provide suitable local pressures on predetermined sections of the patent's spine for posture correction purposes.

In addition, the posture correction girdle 20 of this embodiment further comprises a pair of elastic shoulder straps 26, an elastic waist strap 28 and a crotch 30. Each elastic shoulder strap 26 has one end disposed to the upper portion of the body wrapping shell 22 and the crotch 30 has one end disposed to the bottom portion of the body wrapping shell 22. Furthermore, the elastic waist strap 28 is disposed to the middle back portion of the body wrapping shell 22.

The following demonstrates the customizability of the posture correction girdle 20. A patient suffered from spinal deformity has a curved spine which has at least one section bent away from the dorsal line. The curved spine can be in any pattern, for example, C-shaped and S-shaped. The paddings 32a, 32b, 32c, 32d, 32e, 32f are selectively inserted into the corresponding pockets 24a, 24b, 24c, 24d, 24e, 24f respectively. During use, the padding(s) is put into the pocket(s), which is at a corresponding position(s) of a bent section(s) of the patient's spine. At least one pressure is thereby exerted onto the at least one corresponding section (i.e. bent section) of patient's spine when the posture correction girdle 20 is worn. The exerted pressure induces a corrective force which pushes the bent section of the patient's spine towards the dorsi line to achieve the posture correction purposes.

In one embodiment, the combination of pockets 24a, 24d and corresponding paddings 32a, 32d are configured to provide correction force to the thoracic part; while the combination of pockets 24b, 24c, 24e, 24f and corresponding paddings 32b, 32c, 32e, 32f are configured to provide correction force to the lumber part of the patient.

The following are the two illustrative examples to further illustrate the customizability of the posture correction girdle 20:

The first example is to treat a patient whose spine show a S-shape curve crossing the dorsal line. The curve is characteristized by having a more rigid and larger lumbar curve comparing with the thoracic curve. In order to provide an optimal treatment, in another words an optimal pressure profile, for this patient, paddings 32b, 32c and 32d are inserted into corresponding pockets 24b, 24c and 24d. When the posture correction girdle 20 is worn by the patient, pressures, thereby compressive corrective forces, with opposite directions will be exerted onto the thoracic and lumbar curves respectively to push the bent sections of the spine towards the dorsal line. Moreover, the pressure exerted onto the lumbar curves is greater than that exerted onto the thoracic curves due to this specific arrangement of paddings 32 to deal with the specific characteristics of the patient's spine.

In another illustrative example of patient whose spine also shows a S-shape, but with thoracic curve being larger than the lumbar curve, physicians can insert paddings 32c, 32d and 32e into corresponding pockets 24c, 24d and 24e. In this way, the pressures exerted onto the lumbar and thoracic curve are in opposite directions and the pressure exerted onto the thoracic spine is greater than that onto the lumbar spine and the two pressures.

Figure 2:
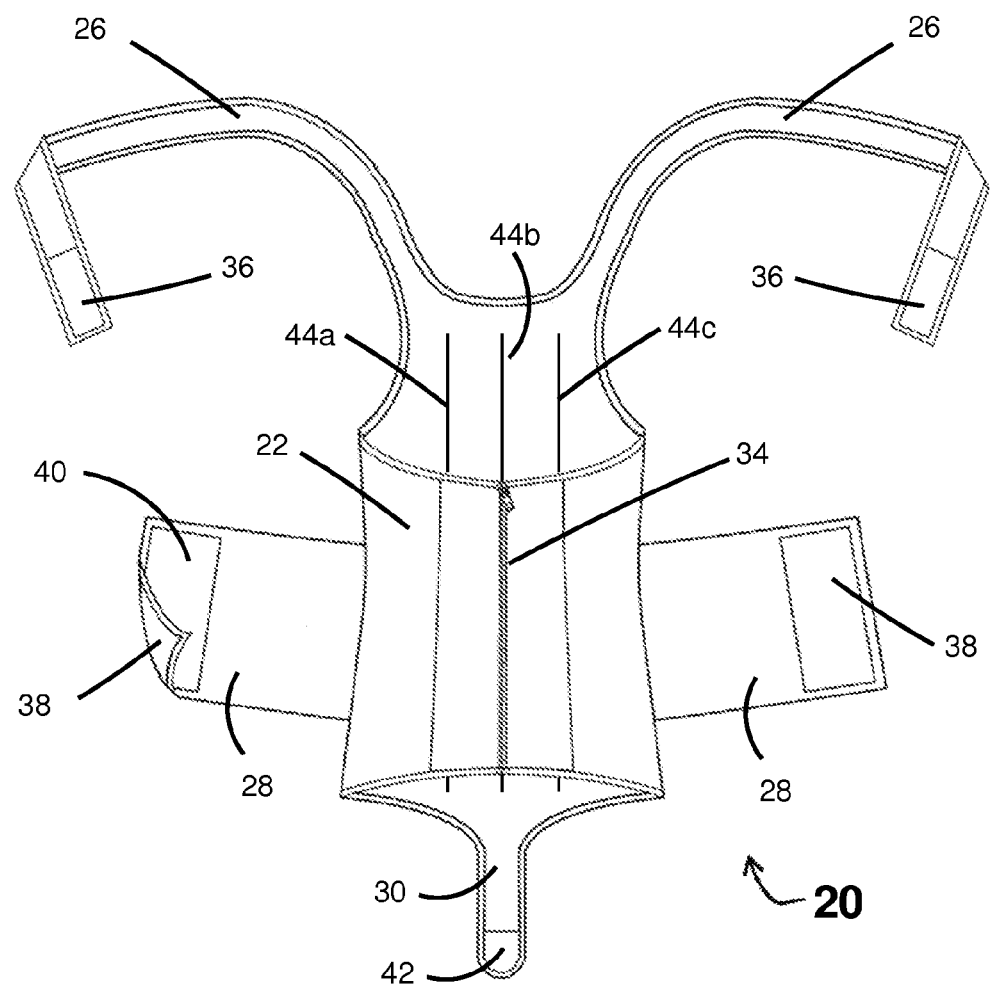
FIG. 2 is a front perspective view of the posture correction girdle when the body wrapping shell is zipped up according to the same embodiment of the present invention.

Referring now to FIG. 2, the posture correction girdle 20 further comprises a zipper 34 in the front portion of the body wrapping shell 22 such that the middle portion of body wrapping shell 22 will surround the user's waist when the zipper 34 is zipped. At the extended end of each elastic shoulder strap 26, there is a first coupling means 36 for coupling the extended end of the two elastic shoulder straps 26 together. For the elastic waist strap 28, there is a second coupling means 38 in both ends which is used for coupling the two ends of the elastic waist strap 28 together during use. In one of the extended end of the elastic waist strap 28, there is a third coupling device 40 which is located at the opposite side of the second coupling means 38 for coupling that extend end of the elastic waist strap 28 to the front portion of the body wrapping shell 22. At the extended end of the crotch 30, there is a fourth coupling means 42 for coupling the crotch 30 to the front portion of the body wrapping shell 22. In a specific embodiment, the coupling means mentioned above are Velcro tape design.

The body wrapping shell 22 further comprises a plurality of elongated bones 44 longitudinally disposed from the upper portion to the lower portion of the body wrapping shell 22. The elongated bones 44 are arranged in a configuration to support the user's spine when the posture correction girdle 20 is worn by the user. In one embodiment, the elongated bones 44 concentrates at the back portion of the body wrapping shell 22 in order to prevent the bending tendency of the user's spine in the sagittal plane.

Figure 3A:
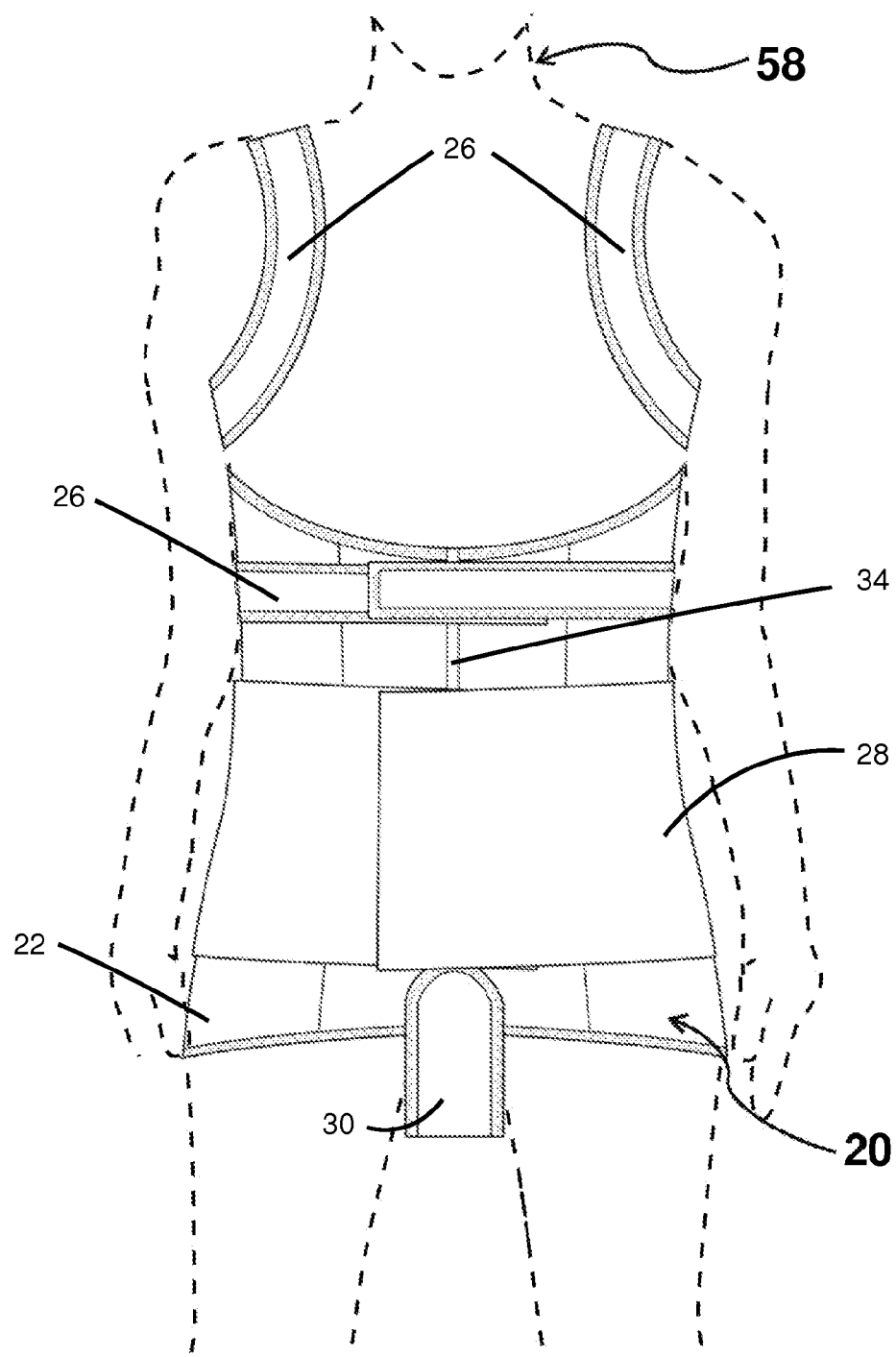
FIG. 3a is a front view of the posture correction girdle with all the straps wrapped in their intended position when worn on a user according to the same embodiment of the present invention.
Figure 3B:
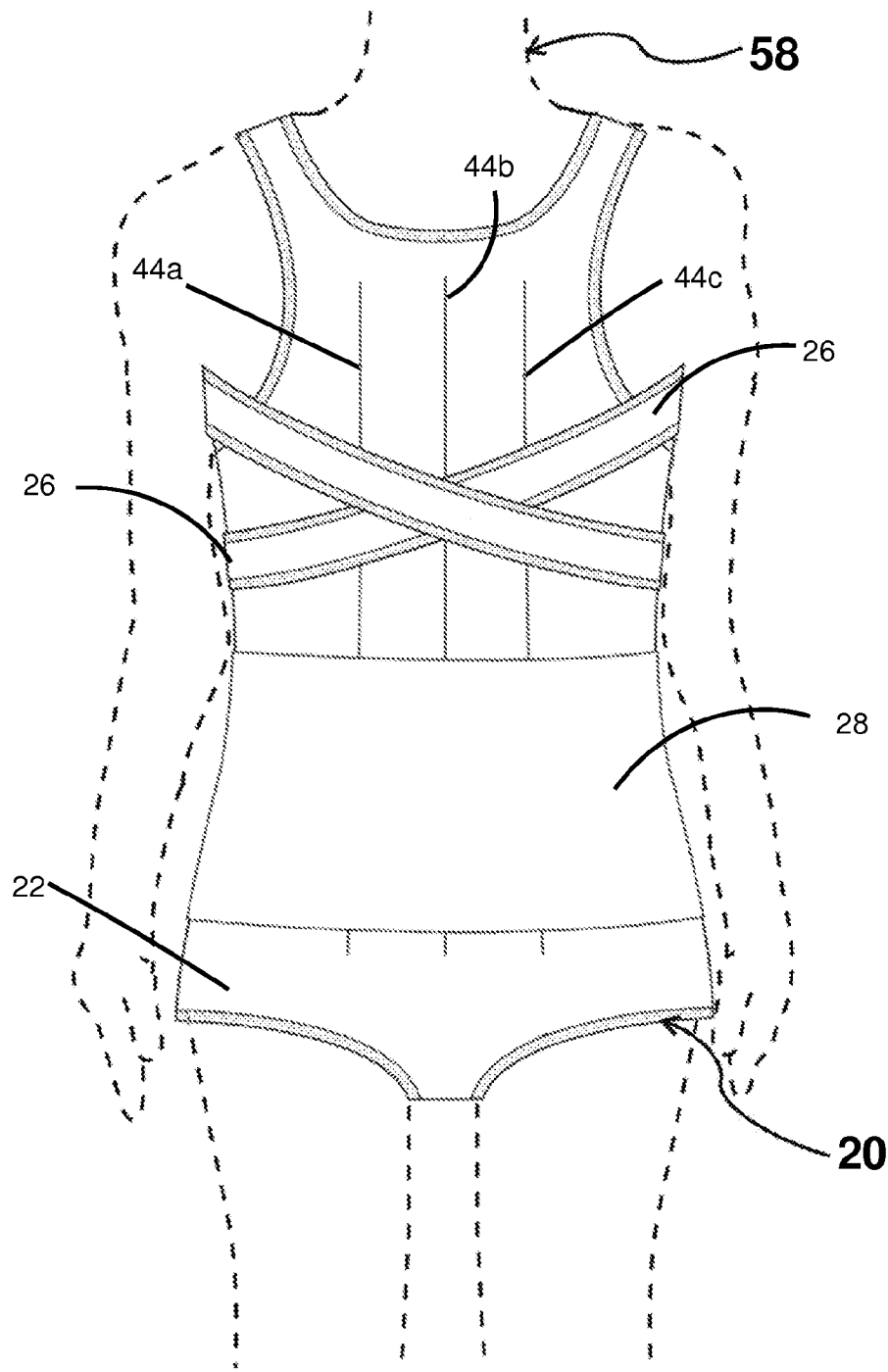
FIG. 3b is a back view of the posture correction girdle in use with all the straps wrapped in their intended position during use by a user according to the same embodiment of the present invention.

Now turning to the wearing procedure of the posture correction girdle 20 described above, FIGS. 3a and 3b show front view and back view of the posture correction girdle 20 when it is in a fully strapped configuration that is typically the position in use by a user 58. To arrive at the fully strapped configuration, the zipper 34 of the body wrapping shell 22 is first zipped so that the body wrapping shell 22 can cover the shoulder, back, waist, pelvis and hip of the user 58. The elastic shoulder straps 26 are then wrapped around the shoulders of the user 58. The elastic shoulder straps 26 are first wrapped from the top to the front of the shoulders of the user 58. Afterwards, the elastic shoulder straps 26 are passed through the underarm and across to the back of the user 58 and wrapped towards to the opposite sides of the user 58 at the outer back portion of the body wrapping shell 22. The elastic shoulder straps 26 are then wrapped around the rib of the user 58 and finally coupled with each other in the front portion of the body wrapping shell 22. These wrapping and elastic extending actions of the elastic shoulder straps 26 generate corrective forces to the upper back of the user 58 for reducing the forward bending tendency of the shoulders in the sagittal plane.

Regarding the elastic waist strap 28, it is used to wrap around the waist of the user 58. In order to provide stable corrective forces, one portion of the elastic waist strap 28 is first wrapped around one side of the user's waist and the corresponding extended end is attached to the front portion of the body wrapping shell 22; following by wrapping the another side of the user's waist using the opposite portion of the elastic waist strap 28. The two portions of the elastic waist strap 28 are coupled with each other in the front portion of the body wrapping shell 22. The wrapping and elastic extending action of the elastic waist strap 28 limits the movement of the pelvis and lumber of the user 58 in the coronal plane. Finally, the crotch 30 is also coupled to the front portion of the body wrapping shell 22 to further limit any undesired movement of the user's pelvis and lumber and to reduce the problem of unlifting or displacement of the posture correction girdle 20 on the body during the movement when in use. Thus, giving optimum performance on posture correction.

Figure 4:
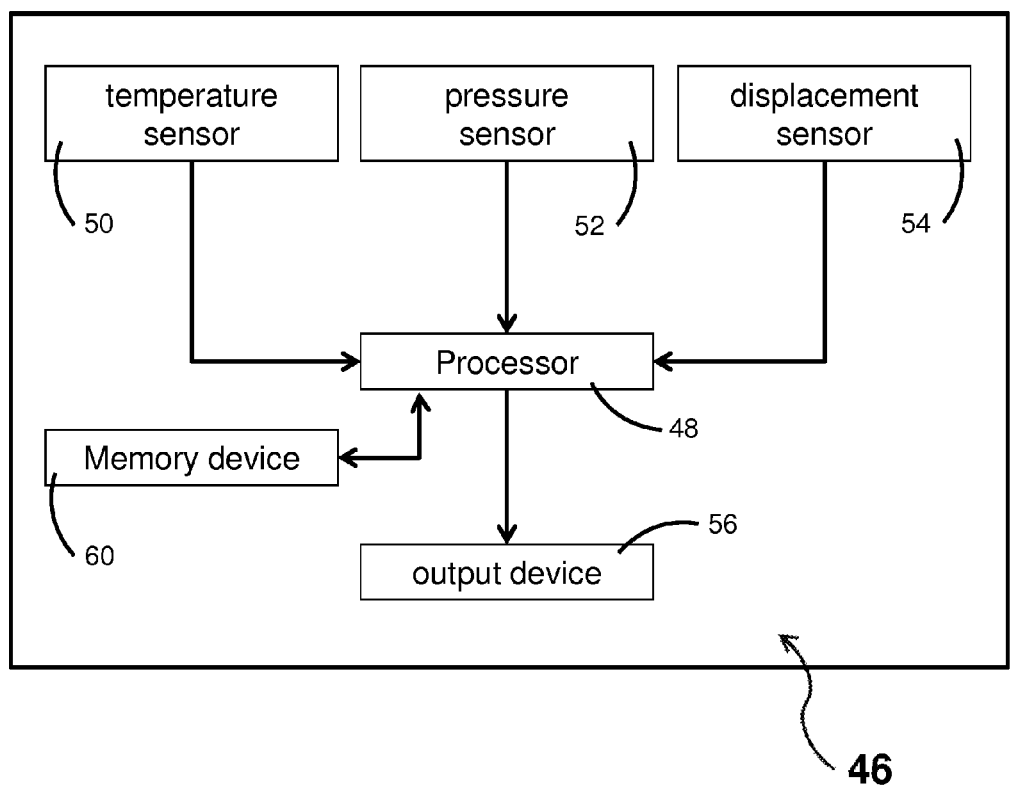
FIG. 4 is a block diagram of the micro-system embedded into the posture correction girdle according to another aspect of the present invention.

In another aspect, the present invention is a posture correction girdle embedded with a micro-system. The posture correction girdle in this aspect could be the same as the one described in the above aspect, and will not repeat here. In one of the embodiments, as shown in FIG. 4, the micro-system 46 comprises a processor 48, a temperature sensor 50, a pressure sensor 52, a displacement sensor 54 and an output device 56. The data acquired by the temperature sensor 50, pressure sensor 52, and displacement sensor 54 are fed into in the processor 48. The processor 48 analyzes and maintains a record thereof regarding the efficiency of the posture correction girdle 20 and the treatment. The aforesaid information is then used to inform the users via the output device 56.

In one embodiment, the efficiency of the posture correction girdle 20 is determining through comparing the signals received from the temperature sensor 50, pressure sensor 52, and displacement sensor 54 are compared with corresponding predetermined values stored in the memory device 60 which is connected to the processor 48. When the received signal deviates from the predetermined values, it indicates the posture correction girdle 20 may not be worn properly or the configuration of the posture correction girdle 20 is inappropriate for a particular patient. In the aforesaid scenarios, a notification will be provided to the user through the output device 56.

In one specific embodiment, the temperature sensor 50 is inserted between the body wrapping shell 22 and the user's skin. The temperature sensor 50 is configured to monitor the wearing practices of the users in an objective way. The data captured by the temperature sensor 50 indicate the thermal confort and the duration of wearing of the posture correction girdle 20.

In another specific embodiment, the pressure sensor 52 is configured to record the pressure profile exerted onto the user's spine. The obtained pressure profile can assist physicians adjust the length of the elastic shoulder straps 26 and elastic waist strap 28 and the position of paddings 32 accordingly. This feedback loop ensures optimal pressure profile is exerted onto the user's spine throughout different stages of the posture correction treatment.

In another specific embodiment, the displacement sensor 54 is configured to determine the position and severity of the user's spinal deformity. In one implementation, two set of sensors are embedded into the posture correction girdle 20: one along the dorsal line and the other one along the midaxillary line of the user. The displacement sensor 54 along the dorsal line is configured to measure the bending angle of the spine in the sagittal plane, while the one along the midaxillary line is configured to measure the bending angle of the spine in the cornal plane. The spinal deformity information obtained by the displacement sensor 54 is compared with previous information stored in the processor 48 to provide a qualitative monitoring of the posture correction treatment.

In another specific embodiment, the output device 56 is a light-edmitting diode (LED). When the data obtained by the temperature sensor 50, the pressure sensor 52 and/or the displacement sensor 54 deviate from the pre-determined values, the LED will light up indicating that the wearing or the configuration of the posture correction girdle 20 is inappropriate.

In another specific embodiment, the output device 56 further is a wireless transmission means which is configured to tranfer the data obtained by the temperature sensor 50, the pressure sensor 52 and/or the displacement sensor 54 to the user's mobile devices for real-time monitoring or to any computing device or display or notification device for monitoring purposes. In another specific embodiment, the wireless transmission means can be mobile wireless networks, Wi-Fi, Bluetooth and/or NFC.

In another specific embodiment, the output device 56 is a removable memory device. All the data obtained by the temperature sensor 50, the pressure sensor 52 and/or the displacement sensor 54 are recorded into the removable memory device. In addition, all the data generated by the micro-system 46 can be recorded into the removable memoey device as well. The removable memory device can be removed and the recorded data can be downloaded into any computing device for other monitoring purposes. In another specific embodiment, the removable momory device can be memory flash drive and/or memory card.

In the third aspect of the present invention, it provides a method for correcting spinal deformity. The method comprises the step of providing a posture correction girdle, wrapping the posture correction girdle around a user and selectively exerting pressure onto predetermined sections of the user's spine through the posture correction girdle. Using this method, corrective forces are exerted on that particular predetermined spine section to achieve spinal deformity correction purposes.

In another embodiment, the method further includes the step of electronically monitoring and providing feedback to the user regarding the efficiency of the correction method.

In one illustrative example, the electronically monitoring is achieved by disposing a temperature sensor onto the posture correction girdle. The data acquired by the temperature sensor is compared with a predetermined value, for instance the body skin temperature (36-37°C.). When the detected temperature falls below the body skin temperature, a notification is provided to the physicians or parents of the patient through output device 56. Thereby, the physicians would be aware of the fact that the posture correction girdle is not being worn at that moment.

In another illustrative example, a pressure sensor is provided and a benchmark pressure profile is inputted by the physician during the examination of patient. When the pressure profile detected by the pressure sensor deviates from that optimal pressure profile, a notification is provided to the user through the output device 56 indicating that the wearing of the posture correction girdle may not be appropriate.

In another illustrative example, displacement sensor is provided and the spinal curvature of user before wearing the posture correction girdle is inputted as a predetermined value. When the detected curvature is greater than the predetermined curvature, a notification will be sent to the user and physicians through the output device 56 indicating that the configuration of the posture correction may not be appropriate.

The exemplary embodiments of the present invention are thus fully described. Although the description referred to particular embodiments, it will be clear to one skilled in the art that the present invention may be practiced with variation of these specific details. Hence, this invention should not be construed as limited to the embodiments set forth herein.

For example, although only six pockets 24 and corresponding paddings 32 are mentioned above, it is clear that the number of pockets 24 and paddings 32 can be adjusted according to a particular spinal deformity. Furthermore, it is clear that the pockets 24 can be disposed at any predetermined position according to the needs of the user, physician or manufacturer.

The first coupling means 36, the second coupling means 38, the third coupling means 40 and the fourth coupling means 42 can be buttons, buckle or zippers.

In the embodiment described above, the elongated bones are concentrates at the back part and side part, which includes both side back part and side front part, of the body wrapping shell 22. It is clear that set of bones may be applied to the elastic shoulder straps 26 in order to reduce the problem of winkles and curling during wearing.

The output module 56 can be any electronic components that can indicate the efficiency of the posture correction girdle 20 and the progression of the posture correction treatment, for example but not limited to display panel and sound emitting devices.

In yet another specific embodiment, the pressure sensing module 52 can be an array of resistive pressure sensors made of a conductive paste interposed between two insulating sheets. The paste is applied so as to form a 6×16 cell grid on one side and a 6×4 cell grid on the other.

The material used to make the body wrapping shell can be any textile, for example cotton, polyester, polyvinyl chloride (PVC), keratin fibers, wool, Spandex, Tencel, acrylic, bamboo fiber, flax, lyocell, rayon, cellulosic acetates, COOLMAX, tricot, satinette, and powernet. In other instances, the paddings can be made from foam and plastic while the elongated bone can be made from resin and plastic.

What is claimed is:

1. A posture correction girdle that corrects a curved spine of a person, the posture correction girdle comprising:
   a body wrapping shell that wraps around the person and includes a front portion with two elastic shoulder straps that wrap around shoulders of the person, a waist portion with an elastic strap that wraps around a waist of the person, and a back portion with pockets that are adjacent a dorsal line of a back of the person such that two of the pockets are vertically positioned on a first side of the dorsal line and two of the pockets are vertically positioned on a second side of the dorsal line;
   a plurality of pads that removably insert into and out of the pockets and have a shape corresponding to a shape of the pockets such that the pads apply a corrective force against the curved spine of the person;
   a first displacement sensor positioned with the body wrapping shell on the first side of the dorsal line, wherein the first displacement sensor measures a bending angle of the curved spine from pressure exerted on the curved spine of the person while the person wears the posture correction girdle; and
   a second displacement sensor positioned with the body wrapping shell on the second side of the dorsal line, wherein the second displacement sensor measures a bending angle of the curved spine from pressure exerted on the curved spine of the person while the person wears the posture correction girdle.

2. The posture correction girdle of claim 1, wherein the body wrapping shell further includes:
   one pocket on the back portion and being vertically aligned with the two pockets that are vertically positioned on the first side of the dorsal line; and
   another pocket on the back portion and being vertically aligned with the two pockets that are vertically positioned on the second side of the dorsal line.

3. The posture correction girdle of claim 1, wherein the body wrapping shell further includes:
   two pockets for a total of six pockets on the back portion, wherein a first one of the six pockets is located on an upper portion of the back portion on the first side of the dorsal line, a second one of the six pockets is located on a middle portion of the back portion on the first side of the dorsal line, a third one of the six pockets is located on a lower portion of the back portion on the first side of the dorsal line, a fourth one of the six pockets is located on the upper portion of the back portion on the second side of the dorsal line, a fifth one of the six pockets is located on the middle portion of the back portion on the second side of the dorsal line, and a sixth one of the six pockets is located on the lower portion of the back portion on the second side of the dorsal line.

4. The posture correction girdle of claim 1, wherein a first set of the pads insert into the pockets to provide corrective force to a thoracic portion of the curved spine of the person, and a second set of pads insert into the pockets to provide corrective force to a lumbar portion of the curved spine of the person.

5. The posture correction girdle of claim 1, wherein the pockets and the pads are located on the back portion of the girdle to push bent sections of the curved spine of the person toward the dorsal line.

6. The posture correction girdle of claim 1, wherein the body wrapping shell further includes:
   an elongated vertical zipper that extends along the front portion; and
   a crotch section that extends outwardly from the back portion and wraps around a crotch of the person and connects to the waist portion.

7. The posture correction girdle of claim 1, further comprising:
   a temperature sensor with the body wrapping shell, wherein the temperature sensor measures a duration that the person wears the posture correction girdle.

8. A method to correct a curved spine of a person, the method comprising:
providing a posture correction girdle that includes a body wrapping shell that wraps around the person and includes a front portion that fits to a front of the person and back portion that fits to a back of the person such that the back portion includes pockets on each side of a dorsal line of the back of the person;
providing a plurality of pads that removably insert into and out of the pockets;
providing, with a first combination of the pads inserted into the pockets, a corrective force to a thoracic portion of the curved spine to push the curved spine at the thoracic portion towards the dorsal line of the back of the person; and
providing, with a second combination of the pads inserted into the pockets, a corrective force to a lumbar portion of the curved spine to push the curved spine at the lumbar portion towards the dorsal line of the back of the person.

9. The method of claim 8 to correct the curved spine of the person, the method further comprising:
providing, with the pads inserted into the pockets, corrective compressive forces with opposite directions exerted onto thoracic and lumbar curves of the curved spine to push bent sections of the curved spine towards the dorsal line and correct for a S-shaped curve of the curved spine.

10. The method of claim 8 to correct the curved spine of the person, the method further comprising:
providing, with the pads inserted into the pockets, corrective compressive forces to correct for a S-shaped curve of the curved spine with a thoracic curve being larger than a lumbar curve such that the pads exert pressure in opposite direction to a lumbar portion of the spine and a thoracic portion of the spine with greater pressure onto the thoracic portion of the spine than the lumbar portion of the spine.

11. The method of claim 8 to correct the curved spine of the person, the method further comprising:
providing, with the pads inserted into the pockets, corrective compressive forces to correct for a S-shaped curve of the curved spine with a lumbar curve being larger than a thoracic curve such that the pads exert pressure in opposite direction to a lumbar portion of the spine and a thoracic portion of the spine with greater pressure onto the lumbar portion of the spine than the thoracic portion of the spine.

12. The method of claim 8 to correct the curved spine of the person, the method further comprising:
monitoring, with a temperature sensor in the posture correction girdle, a duration of time that the person wears the posture correction girdle; and
measuring, with a displacement sensor in the posture correction girdle, a bending angle of the curved spine.

13. A method to correct a curved spine of a person, the method comprising:
providing a posture correction girdle that includes a body wrapping shell that wraps around the person and includes a front portion with two elastic shoulder straps that wrap around shoulders of the person, a waist portion with an elastic strap that wraps around a waist of the person, and a back portion with pockets that are adjacent a dorsal line of a back of the person such that the pockets are symmetrically positioned on each side of a dorsal line of the back of the person;
providing a plurality of pads that removably insert into and out of the pockets; and
providing, by the pads inserted into the pockets, a corrective force to a thoracic portion and to a lumbar portion of the curved spine to push the curved spine towards the dorsal line of the back of the person.

14. The method of claim 13 further comprising:
providing, by the pads inserted into the pockets, corrective compressive forces with opposite directions exerted onto the thoracic portion and onto the lumbar portion to push bent sections of the curved spine towards the dorsal line in order to correct for a C-shaped curve of the curved spine.

15. The method of claim 13 further comprising:
providing, by the pads inserted into the pockets, corrective compressive forces with opposite directions exerted onto the thoracic portion and onto the lumbar portion to push bent sections of the curved spine towards the dorsal line in order to correct for a S-shaped curve of the curved spine.

16. The method of claim 13 further comprising:
providing, by the pads inserted into the pockets, corrective compressive forces to correct for a S-shaped curve of the curved spine with a thoracic curve being larger than a lumbar curve such that the pads exert pressure in opposite direction to the lumbar portion of the spine and to the thoracic portion of the spine with greater pressure being exerted onto the thoracic portion of the spine than the lumbar portion of the spine.

17. The method of claim 13 further comprising:
providing, by the pads inserted into the pockets, corrective compressive forces to correct for a S-shaped curve of the curved spine with a lumbar curve being larger than a thoracic curve such that the pads exert pressure in opposite direction to the lumbar portion of the spine and to the thoracic portion of the spine with greater pressure being exerted onto the lumbar portion of the spine than the thoracic portion of the spine.

18. The method of claim 13 further comprising:
monitoring, with a temperature sensor in the posture correction girdle, a duration of time that the person wears the posture correction girdle; and
measuring, with a displacement sensor in the posture correction girdle, a bending angle of the curved spine.

* * * * *